(12) United States Patent
Emoto et al.

(10) Patent No.: US 10,475,252 B2
(45) Date of Patent: Nov. 12, 2019

(54) IMAGE DIAGNOSIS ASSISTANCE APPARATUS, CONTROL METHOD, AND PROGRAM

(71) Applicant: CANON KABUSHIKI KAISHA, Tokyo (JP)

(72) Inventors: Yutaka Emoto, Kyoto (JP); Hiroyoshi Isoda, Kyoto (JP); Yoshio Iizuka, Takatsuki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 13 days.

(21) Appl. No.: 15/506,860

(22) PCT Filed: Aug. 31, 2015

(86) PCT No.: PCT/JP2015/004391
§ 371 (c)(1),
(2) Date: Feb. 27, 2017

(87) PCT Pub. No.: WO2016/035310
PCT Pub. Date: Mar. 10, 2016

(65) Prior Publication Data
US 2017/0256101 A1 Sep. 7, 2017

(30) Foreign Application Priority Data

Sep. 5, 2014 (JP) ................. 2014-181592

(51) Int. Cl.
*G06T 19/20* (2011.01)
*A61B 5/00* (2006.01)
(Continued)

(52) U.S. Cl.
CPC ............ *G06T 19/20* (2013.01); *A61B 5/0015* (2013.01); *A61B 5/742* (2013.01); *G06F 3/013* (2013.01);
(Continued)

(58) Field of Classification Search
CPC ....................................... G06F 3/013
See application file for complete search history.

(56) References Cited

U.S. PATENT DOCUMENTS

2004/0254763 A1  12/2004  Sakai et al. ............. 702/184
2007/0229660 A1  10/2007  Yamaguchi ............. 348/143
(Continued)

FOREIGN PATENT DOCUMENTS

JP          03202961 A * 9/1991
JP          2004-188002    7/2004
JP          2007-319327   12/2007

OTHER PUBLICATIONS

Igarashi, T. and K. Hinckley. Speed-Dependent Automatic Zooming for Browsing Large Documents. UIST'00. pp. 139-148, 2000.*

*Primary Examiner* — Grace Q Li
(74) *Attorney, Agent, or Firm* — Venable LLP

(57) ABSTRACT

An image diagnosis assistance apparatus is configured to display a plurality of cross-sectional images on a display unit by sequentially switching the plurality of cross-sectional images; obtain user sight-line information including position information on a display screen of the display unit; and obtain a switching speed for switching the plurality of cross-sectional images. The image diagnosis assistance apparatus is configured to determine an observed area with respect to the plurality of cross-sectional images displayed on the display unit based on the obtained sight-line information and switching speed.

10 Claims, 6 Drawing Sheets

(51) Int. Cl.
*G06F 3/01* (2006.01)
*A61B 5/055* (2006.01)
(52) U.S. Cl.
CPC ........... *A61B 5/0033* (2013.01); *A61B 5/0066* (2013.01); *A61B 5/055* (2013.01); *G06T 2210/41* (2013.01); *G06T 2219/2016* (2013.01)

(56) References Cited

U.S. PATENT DOCUMENTS

| | | | |
|---|---|---|---|
| 2009/0110327 A1* | 4/2009 | Chen | G06T 17/10 382/285 |
| 2009/0237529 A1* | 9/2009 | Nakagomi | H04N 5/144 348/231.99 |
| 2011/0199390 A1 | 8/2011 | Iizuka et al. | 345/619 |
| 2012/0050330 A1 | 3/2012 | Iizuka et al. | 345/641 |
| 2012/0136882 A1 | 5/2012 | Kawagishi et al. | 707/758 |
| 2013/0051646 A1 | 2/2013 | Nakano et al. | 382/131 |
| 2014/0038154 A1* | 2/2014 | Brownlow | G09B 5/06 434/317 |
| 2014/0168056 A1* | 6/2014 | Swaminathan | G06K 9/00604 345/156 |
| 2014/0380247 A1* | 12/2014 | Tecarro | G06F 3/0483 715/863 |
| 2015/0109204 A1* | 4/2015 | Li | G06F 3/011 345/156 |
| 2015/0205451 A1* | 7/2015 | Lee | G06F 3/0481 715/766 |
| 2016/0041733 A1* | 2/2016 | Qian | G06F 19/321 715/771 |
| 2017/0199543 A1* | 7/2017 | Rhee | G02B 27/017 |

* cited by examiner

[Fig. 1]
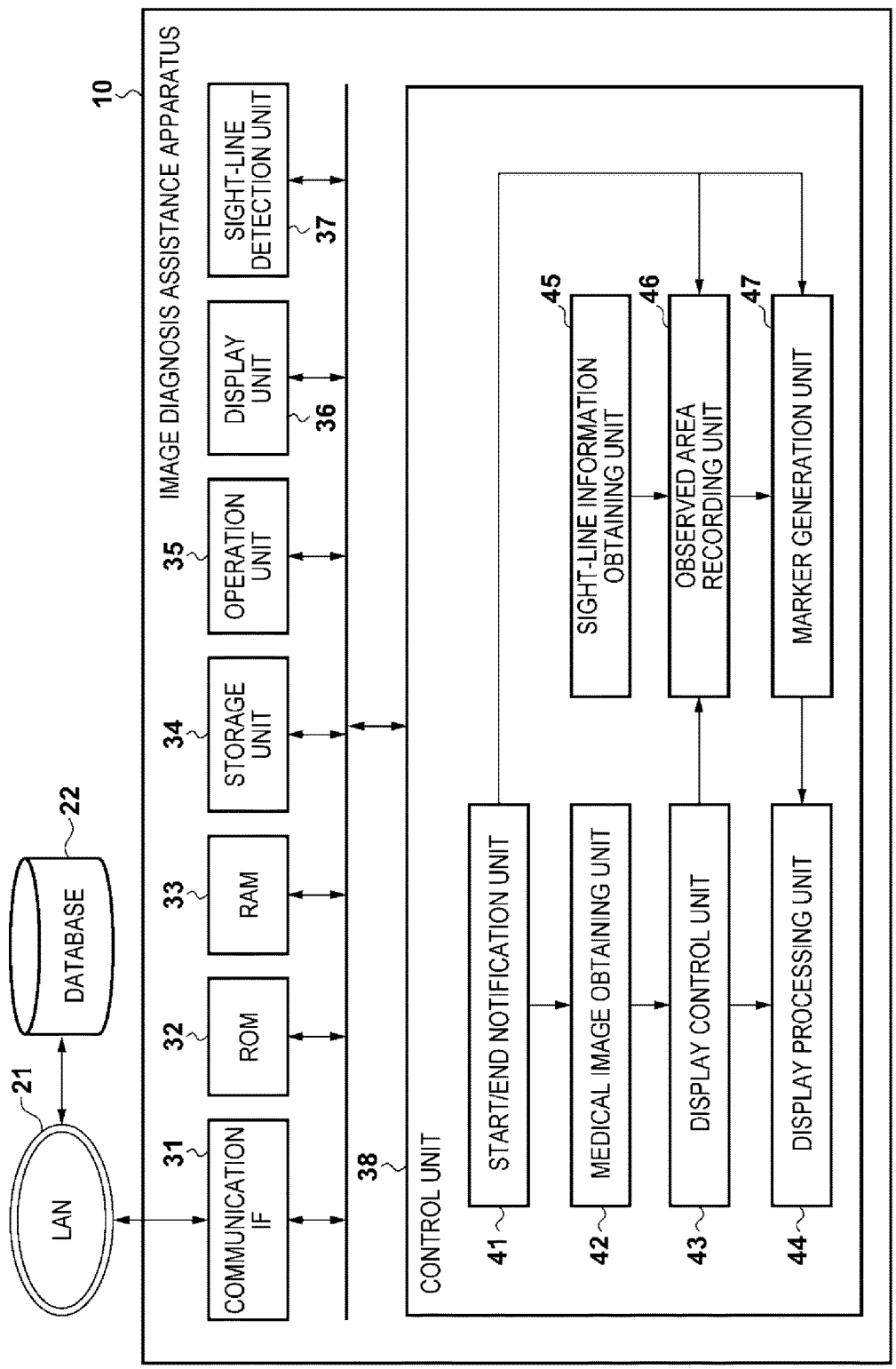

[Fig. 2]
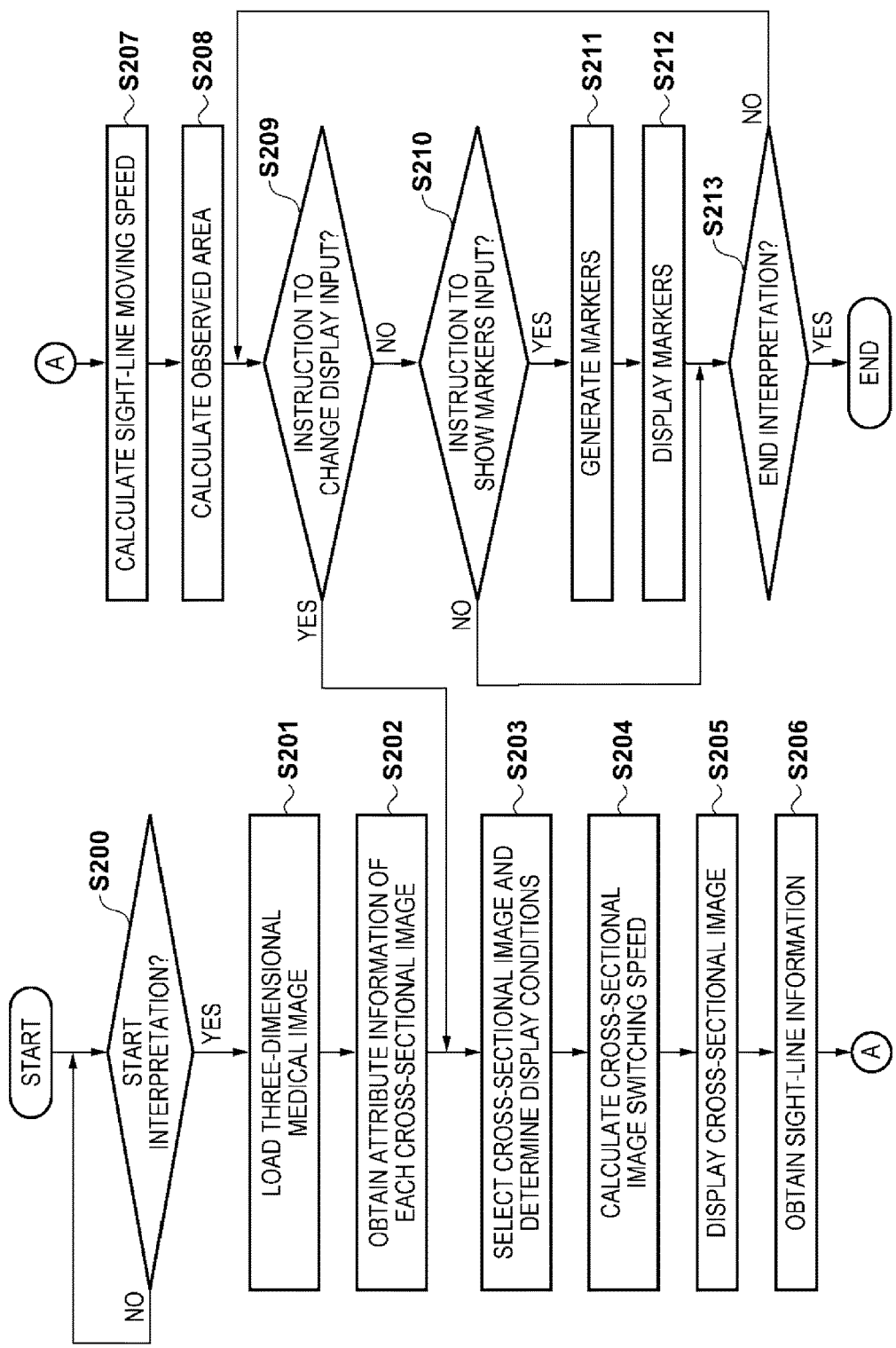

[Fig. 3]
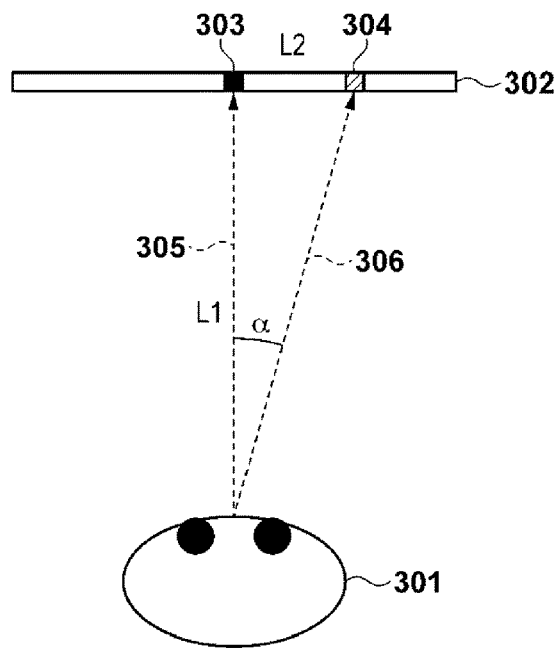
[Fig. 4]
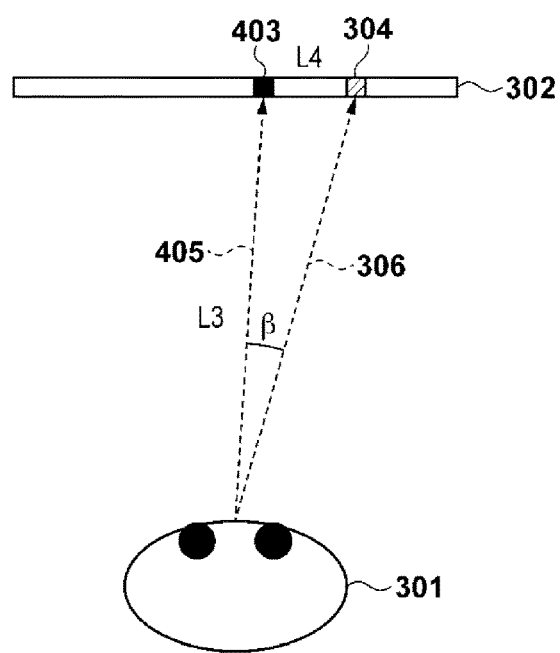

[Fig. 5]
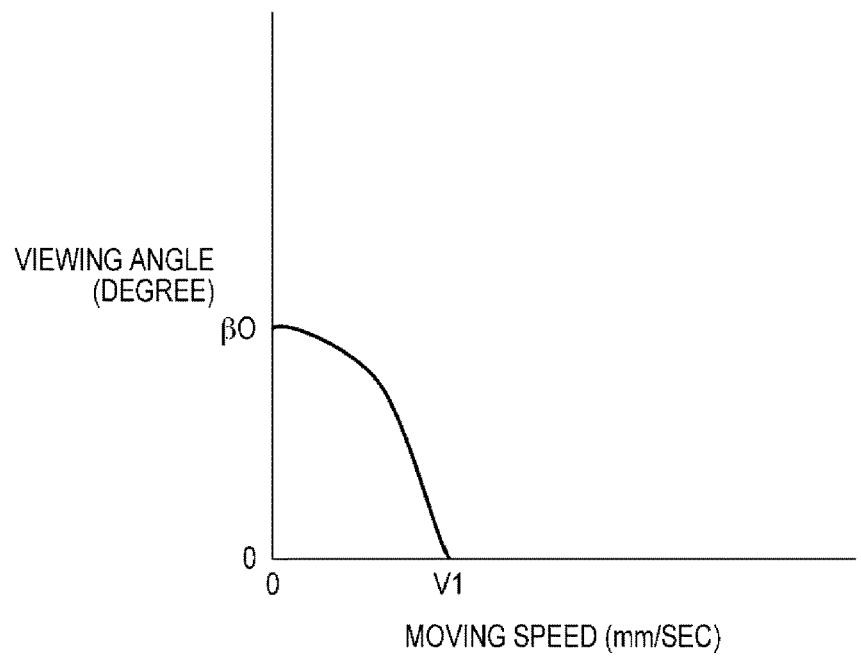
[Fig. 6]
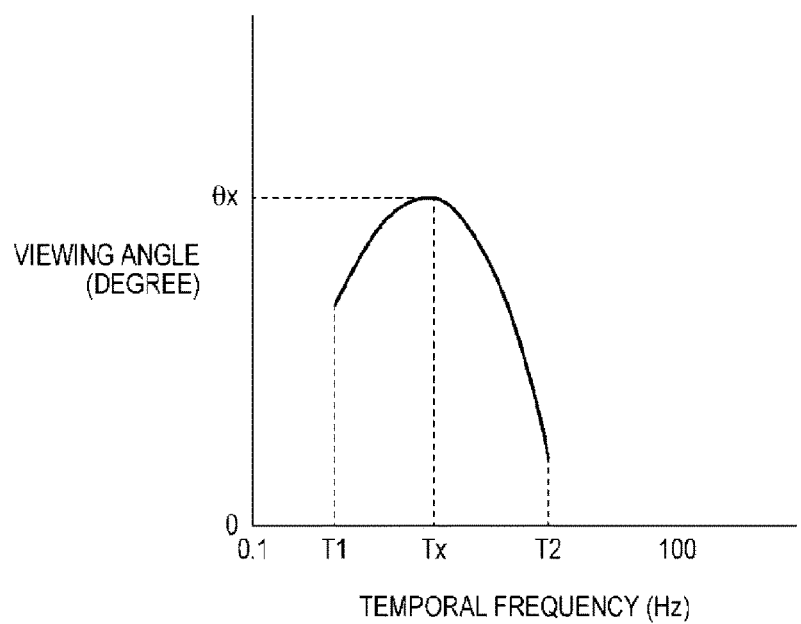

[Fig. 7]

| | | CROSS-SECTIONAL IMAGE SWITCHING SPEED | | |
|---|---|---|---|---|
| | | T1 OR LESS | BETWEEN T1 AND T2 | T2 OR MORE |
| SIGHT-LINE MOVING SPEED | V0 OR LESS | CALCULATE OBSERVED AREA INFORMATION BY USING METHOD SHOWN IN FIG. 3 | CALCULATE OBSERVED AREA INFORMATION BY USING METHOD SHOWN IN FIG. 6 | DETERMINE AS NO FIELD OF VIEW |
| | BETWEEN V0 AND V1 | CALCULATE OBSERVED AREA INFORMATION BY USING METHOD SHOWN IN FIGS. 4 AND 5 | DETERMINE AS NO FIELD OF VIEW | DETERMINE AS NO FIELD OF VIEW |
| | V1 OR MORE | DETERMINE AS NO FIELD OF VIEW | DETERMINE AS NO FIELD OF VIEW | DETERMINE AS NO FIELD OF VIEW |

[Fig. 8]
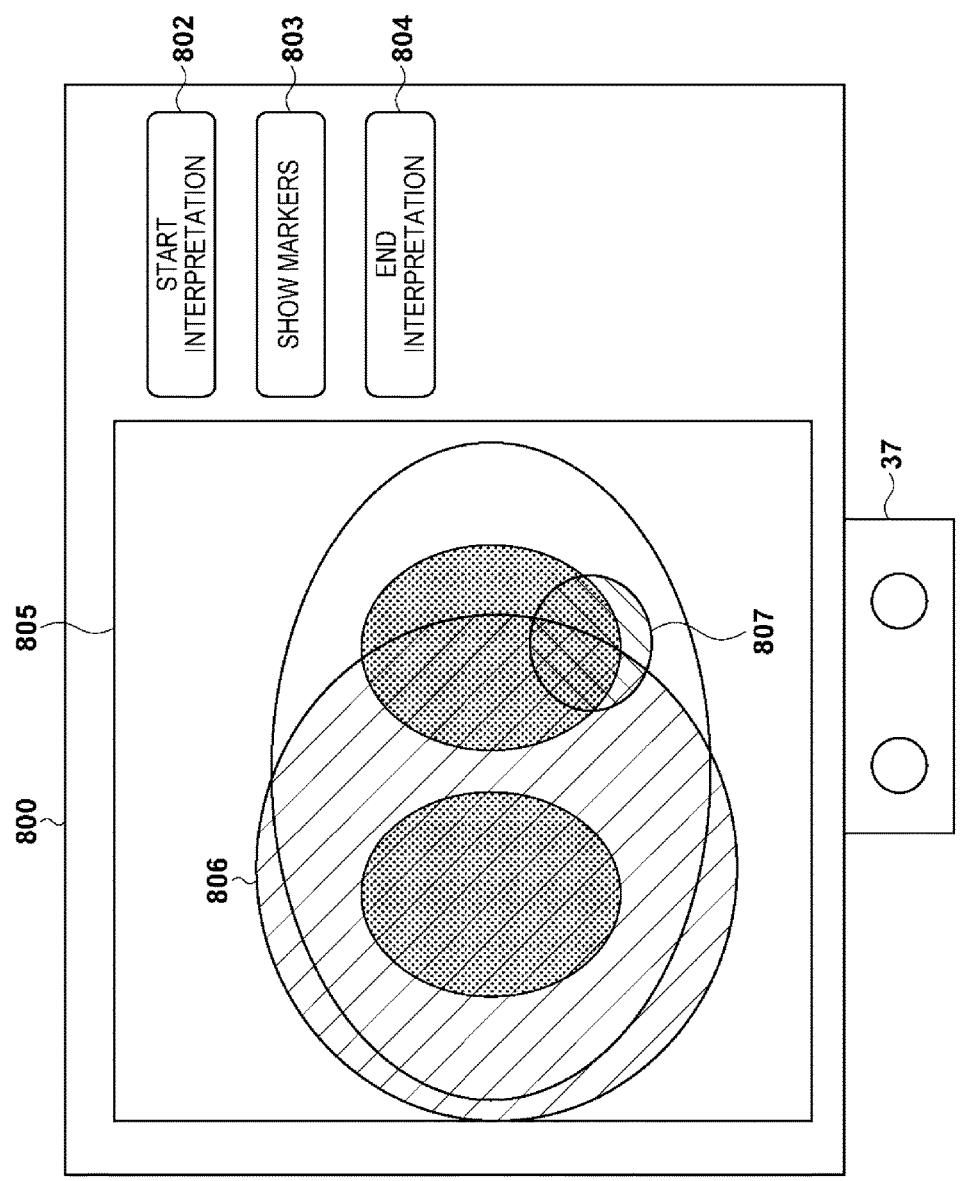

IMAGE DIAGNOSIS ASSISTANCE APPARATUS, CONTROL METHOD, AND PROGRAM

TECHNICAL FIELD

The present invention relates to an image diagnosis assistance apparatus, a control method thereof, and a program.

BACKGROUND ART

At the point of care, three-dimensional medical image data composed of a plurality of cross-sectional images (or slice images) are captured by using medical image capturing apparatuses such as an X-ray CT apparatus, an MRI apparatus and a PET apparatus. When a doctor performs image diagnosis by interpreting the medical image data, it is often the case that a plurality of cross-sectional images are displayed by being sequentially switched. As a result of the cross-sectional images being displayed by being sequentially switched, the doctor can observe the entirety of the three-dimensional medical image data, and find an abnormal shadow that appears in some of the cross-sectional images.

With a recent trend toward an increase in the number of patients due to the aging of population and an increase in the sophistication of medical image capturing apparatuses, the number of tests that require interpretation, the type of medical images taken for a single test, the number of cross-sectional images included in one set of medical images, and image resolution are also increasing. For this reason, a doctor is required to read a large number of cross-sectional images in a limited amount of time, and thus the burden on doctors to interpret medical images is rapidly increasing. As a result, the possibility that a doctor may miss an abnormal shadow in some of the images interpreted (the occurrence of an oversight in interpretation) is increasing more than ever. The occurrence of an oversight in interpretation increases the risk that a doctor may miss an abnormal shadow, leading to a disadvantage for the patients.

Japanese Patent Laid-Open No. 2007-319327 discloses a technique for recording sight-line information of a reader and GUI operations in a time series during interpretation of medical images. With this technique, the system measures and records the sight-line of the reader reading images that need to be interpreted, and thus the reader can identify observed areas observed by the reader and unobserved areas, as a result of which it is possible to indicate an interpretation oversight in the unobserved areas.

The conventional technique described above, however, sets a predetermined range including the center coordinates of the sight-line as focus vision and sets areas in the image where the focus vision has scanned as observed areas, and thus does not give consideration to the fact that the focus vision of the reader changes according to how the reader observes. To be specific, in the case where a doctor is thoroughly observing one cross-sectional image, he/she is gazing at a relatively narrow area, whereas in the case where the doctor is observing a plurality of cross-sectional images for the presence or absence of an abnormal shadow by sequentially switching and displaying the images, he/she is viewing a wider range because of dynamic visual stimulation. Accordingly, with the conventional technique, the reader may not always correctly identify observed areas observed by the reader. In this case, a problem occurs in that an interpretation oversight may be indicated in the observed areas. Or conversely, a problem occurs in that an interpretation oversight may not be indicated in unobserved areas. If such an erroneous indication of interpretation oversight occurs, the reader cannot smoothly perform interpretation of medical images. Accordingly, in order to assist interpretation of medical images, it is an important issue to allow the reader to always appropriately identify observed areas.

SUMMARY OF INVENTION

The present invention has been made in view of the problems described above, and it is an object of the present invention to provide an image diagnosis assistance apparatus and method that can appropriately determine observed areas irrespective of the method of image observation performed by the reader.

According to one aspect of the present invention, there is provided an image diagnosis assistance apparatus comprising: display control means for displaying a plurality of cross-sectional images on a display unit by sequentially switching the plurality of cross-sectional images; first obtaining means for obtaining sight-line information regarding a sight line of a user, the sight-line information including position information on a display screen of the display unit; second obtaining means for obtaining a switching speed for switching the plurality of cross-sectional images; and determination means for determining an observed area with respect to the plurality of cross-sectional images displayed by the display control means based on the sight-line information obtained by the first obtaining means and the switching speed obtained by the second obtaining means.

According to another aspect of the present invention, there is provided an image diagnosis assistance apparatus comprising: display control means for displaying a cross-sectional image on a display unit; first obtaining means for obtaining sight-line information regarding a sight line of a user, the sight-line information including position information on a display screen of the display unit; second obtaining means for obtaining a moving speed of the sight line of the user; and determination means for determining an observed area with respect to the cross-sectional image displayed by the display control means based on the sight-line information obtained by the first obtaining means and the moving speed obtained by the second obtaining means.

According to another aspect of the present invention, there is provided a control method for controlling an image diagnosis assistance apparatus, the method comprising: a display control step of displaying a plurality of cross-sectional images on a display unit by sequentially switching the plurality of cross-sectional images; a first obtaining step of obtaining sight-line information regarding a sight line of a user, the sight-line information including position information on a display screen of the display unit; a second obtaining step of obtaining a switching speed for switching the plurality of cross-sectional images; and a determination step of determining an observed area with respect to the plurality of cross-sectional images displayed in the display control step based on the sight-line information obtained in the first obtaining step and the switching speed obtained in the second obtaining step.

According to another aspect of the present invention, there is provided a control method for controlling an image diagnosis assistance apparatus, the method comprising: a display control step of displaying a cross-sectional image on a display unit; a first obtaining step of obtaining sight-line information regarding a sight line of a user, the sight-line information including position information on a display screen of the display unit; a second obtaining step of obtaining a moving speed of the sight line of the user; and a determination step of determining an observed area with respect to the cross-sectional image displayed in the display control step based on the sight-line information obtained in the first obtaining step and the moving speed obtained in the second obtaining step.

Further features of the present invention will become apparent from the following description of exemplary embodiments with reference to the attached drawings.

BRIEF DESCRIPTION OF DRAWINGS

FIG. 1 is a diagram showing an example of an overall configuration of an image diagnosis assistance system according to an embodiment of the present invention.

FIG. 2 is a flowchart illustrating a processing procedure according to an embodiment of the present invention.

FIG. 3 is a diagram illustrating a method for measuring the field of view while the user is not moving the sight-line.

FIG. 4 is a diagram illustrating a method for measuring the field of view while the user is moving the sight-line.

FIG. 5 is a diagram illustrating a change in the viewing angle while the user is moving the sight-line.

FIG. 6 is a diagram illustrating a change in the viewing angle while the user is observing a graphic whose density value changes with time.

FIG. 7 is a diagram illustrating methods for calculating an observed area.

FIG. 8 is a diagram showing an example of a display screen of a display unit and an example of an installation position of a sight-line detection unit.

DESCRIPTION OF EMBODIMENTS

Hereinafter, an embodiment of the present invention will be described with reference to the drawings. It is to be noted, however, that the scope of the present invention is not limited to the examples illustrated herein. For example, in the following description, an example will be given in which cross-sectional images (for example, computed tomography images) constituting three-dimensional image data are displayed as medical image so as to perform interpretation, but the medical images to be interpreted are not limited thereto. The present invention is applicable to interpretation of various medical images such as ordinary two-dimensional X-ray images, OCT images, cross-sectional images obtained by an ultrasound diagnostic apparatus, and the like.

An image diagnosis assistance apparatus according to the present embodiment obtains medical information (medical images, electronic medical record information and the like) related to a symptom that needs to be diagnosed and input information (user sight-line information, GUI operation information and the like) from the user, so as to assist in making a diagnosis for the symptom. Hereinafter, the present invention will be described by using, as an example, three-dimensional medical image data composed of a plurality of cross-sectional images, but the image diagnosis assistance target is not limited thereto, and the present invention is applicable to any image data as long as a plurality of images are observed. The embodiments described below are merely examples given to describe processing methods performed by the image diagnosis assistance apparatus.

FIG. 1 is a diagram showing an overall configuration of an image diagnosis assistance system including an image diagnosis assistance apparatus according to the present embodiment. The image diagnosis assistance system includes an image diagnosis assistance apparatus 10 and a database 22 which are connected to each other so as to be capable of communication via a communication element. In the present embodiment, the communication element is a local area network (LAN) 21. The database 22 manages data such as medical images. The image diagnosis assistance apparatus 10 obtains medical images managed by the database 22 via the LAN 21. The image diagnosis assistance apparatus 10 includes, as functional constituent elements thereof, a communication IF 31, a ROM 32, a RAM 33, a storage unit 34, an operation unit 35, a display unit 36, a sight-line detection unit 37, and a control unit 38.

In the image diagnosis assistance apparatus 10, the communication IF (interface) 31 is implemented by, for example, a LAN card or the like, and controls communication between the image diagnosis assistance apparatus 10 and an external apparatus (for example, the database 22) via the LAN 21. The read only memory (ROM) 32 is implemented by a non-volatile memory or the like, and stores therein various types of programs and the like. The random access memory (RAM) 33 is implemented by a volatile memory or the like, and temporarily stores therein various types of information. The storage unit 34 is implemented by, for example, a hard disk drive (HDD) or the like, and stores therein various types of information. The operation unit 35 is implemented by, for example, a keyboard, a mouse and the like, and inputs instructions from the user into the apparatus. The display unit 36 includes, for example, a liquid crystal display or the like, and displays various types of information for the user.

The sight-line detection unit 37 is a unit that detects a user sight-line, and is implemented by, for example, a video camera capable of synchronous capturing from a plurality of viewpoints, an eye tracker (sight-line tracking apparatus) or the like. To be more specific, a user face or eyes is captured from a plurality of viewpoints, and predetermined image recognition processing is performed on stereo images obtained by image capturing, so as to detect user sight-line information. To be more specific, the orientation of the user face, the iris position and moving direction of both eyes, and the like are determined on a three-dimensional coordinate system, so as to detect user sight-line information of the user viewing the display unit 36. The sight-line information includes position information indicating the position on the display screen of the display unit 36 at which the user is viewing and distance information between the user and the display unit 36. Then, the sight-line information is detected continuously at a predetermined time interval (for example, every several milliseconds).

The control unit 38 is implemented by, for example, a central processing unit (CPU) or the like, and performs overall control on the processing of the image diagnosis assistance apparatus 10 by executing a program stored in the ROM 32 or the RAM 33. The control unit 38 includes, as functional constituent elements thereof, a start/end notification unit 41, a medical image obtaining unit 42, a display control unit 43, a display processing unit 44, a sight-line information obtaining unit 45, an observed area recording unit 46, and a marker generation unit 47. The functions of the constituent elements of the control unit 38 are implemented by the CPU executing a predetermined program, details of which will be described with reference to the flowchart shown in FIG. 2.

FIG. 2 is a flowchart illustrating a processing procedure according to the present embodiment controlled by the control unit 38 of the image diagnosis assistance apparatus 10.

In step S200, the start/end notification unit 41 waits for a user instruction to start interpretation to be input through the operation unit 35. If an instruction to start interpretation is input from the user, the start/end notification unit 41 notifies at least the medical image obtaining unit 42 and the observed area recording unit 46 of the start of interpretation, and the processing proceeds to step S201. The start/end notification unit 41 notifies, if necessary, other constituent elements in the control unit 38 of the start of interpretation.

In step S201, the medical image obtaining unit 42 loads three-dimensional image data from the database 22 via the communication IF 31 and the LAN 21 based on the user instruction input through the operation unit 35, and stores the loaded image data in the storage unit 34. Then, in step S202, the medical image obtaining unit 42 obtains attribute information of each of a plurality of cross-sectional images included in the three-dimensional image data loaded in step S200, and outputs the obtained attribute information to the display control unit 43. The attribute information of the cross-sectional image also includes storage location information of each cross-sectional image included in the three-dimensional image data stored in the storage unit 34 in step S201.

In step S203, the display control unit 43 selects a cross-sectional image that needs to be displayed based on the user instruction input through the operation unit 35, determines display conditions for displaying the selected cross-sectional image, and outputs the attribute information and the display conditions of the selected cross-sectional image to the display processing unit 44. The display conditions of the image includes display area information of the image on the display unit 36, display position information of the image in the display area, the scaling factor of the image, information indicating whether or not to horizontally or vertically flip the image, the rotation angle of the image, the method for converting the density of the image, and the like.

In the following steps S204 to S207, an observing state in which the medical image displayed on the display screen of the display unit 36 is viewed is determined. In the present embodiment, as an example of determination of the observing state, an example will be described in which a medical image switching speed and a sight-line moving speed are used, but other information may be used to determine the observing state. Alternatively, either one of the switching speed and the moving speed may be used to determine the observing state. First, in step S204, the display control unit 43 calculates a frequency of changes (switching speed) of cross-sectional images, and outputs the calculated frequency of changes to the observed area recording unit 46. The calculation of the cross-sectional image switching speed need not necessarily be performed in step S204, and may be performed regularly (periodically) by using a timer interrupt function of the control unit 38. In step S205, the display processing unit 44 loads cross-sectional images from the storage unit 34 based on the attribute information of the cross-sectional images provided from the display control unit 43, and displays the cross-sectional images on the display unit 36 by using the designated display conditions.

In step S206, the sight-line information obtaining unit 45 obtains the sight-line information continuously detected by the sight-line detection unit 37, and outputs the obtained sight-line information to the observed area recording unit 46. As mentioned in the description of the sight-line detection unit 37, the sight-line information includes position information indicating the position on the display screen of the display unit 36 at which the user is viewing and distance information between the user and the display unit 36.

In step S207, the sight-line information obtaining unit 45 calculates the sight-line moving speed based on a change in the sight-line information with time, and outputs the calculated moving speed to the observed area recording unit 46. The sight-line moving speed can be calculated as the amount of change with time in the position information indicating the position on the display screen of the display unit 36 at which the user is viewing. The calculation of the sight-line moving speed need not necessarily be performed in step S207, and may be performed regularly (periodically) by using the timer interrupt function of the control unit 38.

In step S208, the observed area recording unit 46 calculates an area (observed area) in the cross-sectional image where the user observed. At this time, the observed area recording unit 46 calculates the observed area by using the cross-sectional image switching speed calculated in step S204, the sight-line information obtained in step S206, and the sight-line moving speed calculated in step S207. The method for calculating an observed area will be described later. Furthermore, in step S208, the observed area recording unit 46 records the calculated observed area in the storage unit 34 in chronological order.

In step S209, the display control unit 43 checks whether or not a user instruction regarding display has been input through the operation unit 35. If it is determined that a user instruction to change (switch) the displayed cross-sectional image or to change the display conditions of the cross-sectional image has been input, the processing returns to step S203. If, on the other hand, it is determined that a user instruction regarding display has not been input, the processing proceeds to step S210.

In step S210, the start/end notification unit 41 checks whether or not a user instruction to show markers indicating interpreted areas or uninterpreted areas has been input through the operation unit 35. If it is determined that a user instruction to display markers has been input, the start/end notification unit 41 notifies the observed area recording unit 46 and the marker generation unit 47 of execution of a marker display operation, and the processing proceeds to step S211. If, on the other hand, it is determined that a user instruction to show markers has not been input, the processing proceeds to step S213.

In step S211, the observed area recording unit 46 that has received the notification to execute a marker display operation outputs, to the marker generation unit 47, the observed areas calculated and recorded in chronological order in step S208. Furthermore, in step S211, the marker generation unit 47 that has received the notification to execute a marker display operation generates three-dimensional markers to be displayed in a superimposed manner on three-dimensional image data based on the observed areas calculated in step S208, and outputs the generated three-dimensional markers to the display processing unit 44.

As used herein, "three-dimensional marker" refers to a set of two-dimensional markers on each cross-sectional image included in the three-dimensional image data. Likewise, "two-dimensional marker" refers to a graphic or an image for making a distinction between an observed area and an unobserved area in the corresponding cross-sectional image. As an example of the two-dimensional marker, the method of filling an unobserved area with a predetermined color or pattern may be used. The predetermined color or pattern may be changed by a user instruction. In the case of generating a three-dimensional marker, the thickness of a two-dimensional marker (the length in a direction perpendicular to the two-dimensional plane of the cross-sectional image) is set to be equal to, for example, a slice thickness of the cross-sectional image. Alternatively, it is also possible to set an observed area in a predetermined number of consecutive cross-sectional images (for example, to reflect a two-dimensional marker generated in the n-th cross-sectional image in the (n+1)th cross-sectional image and the (n−1)th cross-sectional image).

In step S212, the display processing unit 44 inputs the three-dimensional markers generated in step S211, extracts two-dimensional markers corresponding to the cross-sectional image displayed on the display unit 36 from the three-dimensional markers, and combines the two-dimensional markers with the displayed cross-sectional image by using a predetermined method. For example, the cross-sectional image and the two-dimensional markers are combined with a degree of transparency of 50%. Furthermore, in step S212, the display processing unit 44 displays the combined image obtained in step S212 on the display unit 36. Through the above processing, two-dimensional markers indicating checked areas are displayed in a superimposed manner on the displayed medical image (cross-sectional image).

In step S213, the start/end notification unit 41 determines whether or not a user instruction to end interpretation has been input through the operation unit 35. If it is determined that a user instruction to end interpretation has been input, the processing of FIG. 2 ends. If, on the other hand, it is determined that a user instruction to end interpretation has not been input, the processing returns to step S209, where the above-described processing is repeated.

After execution of step S213, the processing returns to step S209. After that, in the case where the above-described steps S203 to S208 are executed again, the processing of step S205 may be replaced by the processing of step S212 when executed. The user can switch whether or not to replace the processing of step S205 by the processing of step S212. By doing so, the user can observe cross-sectional images having markers displayed in a superimposed manner on the observed areas, and thus can efficiently perform interpretation on only the areas without markers displayed in a superimposed manner, or in other words, unobserved areas. In other words, it is possible to efficiently prevent an oversight in interpretation.

With the above-described processing, at least one of the constituent elements of the control unit 38 may be implemented by an independent apparatus. Alternatively, it may be implemented as software that implements the functions of the constituent elements. Alternatively, at least one of the functions implemented by the control unit 38 may be implemented by cloud computing. To be specific, the above-described processing may be executed by a computation apparatus by connecting, via the LAN 21, the image diagnosis assistance apparatus 10 and the computation apparatus installed in a location different from the location where the image diagnosis assistance apparatus 10 is installed, and performing transmission and reception of data.

The method for calculating an observed area in step S208 of FIG. 2 will be described next with reference to FIGS. 3 to 7. In the present embodiment, the method for calculating an observed area that has been viewed by the user is changed according to a change in the observing state in which the user is viewing the cross-sectional image. For example, the size of the field of view of the user observing the cross-sectional image, or in other words, observable area is changed according to an observing state such as the state in which the sight-line of the user is stationary, the state in which the sight-line is moving, or the state in which the display of cross-sectional image is switched, so as to determine a checked area.

FIG. 3 is a diagram illustrating a method for measuring the field of view while the user is observing a still image, or in other words, while the sight-line is not moving. In FIG. 3, it is assumed that a user 301 is sitting in front of a display screen 302 of the display unit 36, and viewing a gazing graphic 303 displayed in the center of the display screen 302. That is, a sight-line direction 305 of the user 301 directs toward the center (the gazing graphic 303) of the display screen 302. In this state, a graphic 304 having a predetermined shape, size, density pattern and density value is presented on the display screen 302, and then a visual angle $\alpha$ when the user 301 noticed the presence of the graphic is measured. The visual angle $\alpha$ is an interior angle between the sight-line direction 305 and a direction 306 in which the graphic 304 is present.

The visual angle $\alpha$ can be determined from Equation (1) using a trigonometric function if the distance between the user 301 and the center (the position at which the gazing graphic 303 is displayed) of the display screen 302 is represented by L1, and the distance between the center (the position at which the gazing graphic 303 is displayed) of the display screen 302 and the position at which the graphic 304 is presented is represented by L2. In the equation, $\tan^{-1}$ means an arc tangent of the trigonometric function.

$$\alpha = \tan^{-1}(L2/L1) \quad (1)$$

The field of view (circular range) can be determined by measuring a maximum value of the visual angle $\alpha$ (viewing angle $\alpha_{max}$). It is desirable that the viewing angle $\alpha_{max}$ is measured in advance for each user, but a standard viewing angle may be used by omitting the measurement of the viewing angle $\alpha_{max}$ for each user. Furthermore, the viewing angle $\alpha_{max}$ differs slightly between the horizontal direction and the vertical direction, and thus by measuring the viewing angle $\alpha_{max}$ independently in each direction, a more accurate field of view (elliptic range) can be determined.

In step S208 shown in FIG. 2, a distance L2' is calculated from Equation (2) by using a predetermined viewing angle $\alpha_{max}$ set by the above-described method and a distance L1' between the display unit 36 and the user included in the sight-line information obtained in step S206 of FIG. 2. In the equation, tan means a tangent of the trigonometric function.

$$L2' = \tan(\alpha_{max}) * L1' \quad (2)$$

If the field of view of the user on the display screen of the display unit 36 is regarded as a circular area, the observed area can be obtained as a circular area having the radius L2' with the gazing point of the user being set at the center. In the case where the viewing angle $\alpha_{max}$ is measured independently in the horizontal direction and the vertical direction, by separately determining the radius in the horizontal direction and the radius in the vertical direction by using Equation (2), the observed area can be obtained as an elliptic area with the gazing point being set at the center. As described above, the predetermined viewing angle $\alpha_{max}$ is that obtained when the user was observing a still image, and thus even if the distance L1' between the user and the display unit 36 is changed as a result of the user moving the observation position, it is possible to obtain an appropriate observed area according to the distance L1'.

FIG. 4 is a diagram illustrating a method for measuring the field of view while the user is observing a moving graphic, or in other words, while the sight-line is moving. In FIG. 4, the user 301 and the display screen 302 of the display unit 36 are the same as those of FIG. 3, and thus are indicated by the same reference numerals. Also, the graphic 304 having a predetermined shape, size, density pattern and density value is presented on the display screen 302 as in FIG. 3, and the direction, from the user, in which the graphic 304 is present is also represented by reference numeral 306 as in FIG. 3.

In FIG. 4, a major difference from FIG. 3 is that a gazing graphic 403 that can be reliably observed by the user (that has a large contrast difference with the background image) is displayed by being moved at a constant speed. At this time, the graphic 304 is also displayed by being moved at the constant speed so as to maintain the relative position (distance and direction) with respect to the gazing graphic 403. Also, an interior angle (visual angle) between a sight-line direction 405 when the user is gazing the gazing graphic 403 and the direction 306 in which the graphic 304 is present is represented by $\beta$.

Here, the distance between the user and the gazing graphic 403 is represented by L3, and the distance between the gazing graphic 403 and the graphic 304 is represented by L4. Then, the visual angle $\beta$ is measured when the graphic 304 moving together with the gazing graphic 403 at a constant speed is presented, and the user notices the presence of the graphic 304. At this time, if the gazing graphic 403 is controlled so as to move near the center of the display screen 302, the visual angle $\beta$ can be approximately determined from Equation (3) using a trigonometric function.

$$\beta = \tan^{-1}(L4/L3) \quad (3)$$

By measuring a maximum value of the visual angle $\beta$ (viewing angle $\beta_{max}$), the field of view (circular range) while the sight-line is moving can be determined. It is desirable that the viewing angle $\beta_{max}$ is measured in advance for each user, but it is also possible to measure the viewing angles $\beta_{max}$ of a plurality of users in advance, and use the average value thereof as a standard viewing angle. Furthermore, the viewing angle $\beta_{max}$ differs slightly between the horizontal direction and the vertical direction, and thus by measuring the viewing angle $\beta_{max}$ independently in each direction, a more accurate field of view (elliptic range) can be determined.

Also, the viewing angle $\beta_{max}$ is determined with respect to a plurality of different moving speeds of the gazing graphic 403. FIG. 5 is a diagram illustrating a change in the viewing angle with respect to the sight-line moving speed while the user is observing a moving graphic, or in other words, while the sight-line is moving. FIG. 5 can be obtained by measuring, with the use of the method described with reference to FIG. 4, a change in the viewing angle $\beta_{max}$ when the moving speed of the gazing graphic 403 is changed.

In FIG. 5, the vertical axis indicates viewing angle, and the horizontal axis indicates sight-line moving speed. The unit of the viewing angle is degrees (°), and the unit of the moving speed is moving distance/unit time (for example, mm/sec). As shown in FIG. 5, the field of view becomes narrower as the sight-line moving speed increases, and if the moving speed reaches a predetermined threshold value or more (V1 or more), normal observation cannot be performed, and the viewing angle reaches 0° (no field of view).

Next is a description of how the size of the field of view is determined based on the switching speed when the display of cross-sectional image is switched. FIG. 6 is a diagram illustrating a change in the viewing angle while the user is observing a graphic whose density value changes with time. Generally, when a person is observing a stationary object, the sight-line position is substantially fixed, and the range of the field of view is a relatively narrow range called "central vision". On the other hand, when a person is observing a moving object, it is known that the person can see a chronological change of the observed object in a wide range of the field of view called "peripheral vision", with the sight-line position being substantially fixed. The change in the viewing angle when the display of cross-sectional image is switched during interpretation is, in principle, the same as in the example shown in FIG. 6.

In FIG. 6, the vertical axis indicates viewing angle, and the horizontal axis indicates temporal frequency. The unit of the viewing angle is degrees (°), and the unit of the temporal frequency is hertz (Hz). In order to measure visual characteristics of FIG. 6, an image observation method, which is substantially the same as that of FIG. 3, is used. However, in the description of FIG. 3, a still image is presented as the graphic 304, but in the measurement of visual characteristics of FIG. 6, the graphic 304 is periodically changed between a displayed state and a hidden state. At this time, the degree of transparency of the graphic 304 displayed in a superimposed manner on the background image is changed as follows in one period: 100% (transparent)→0% (opaque)-->100% (transparent). Also, at this time, the degree of transparency of the graphic 304 is changed in the same manner as the sinusoidal waveform of a trigonometric function. The graphic 304 whose density is periodically changed with time in the manner as described above is presented to the user, a visual angle $\Theta$ when the user notices the presence of the graphic is measured, and a maximum value $\Theta_{max}$ of the visual angle $\Theta$ is defined as the viewing angle.

As shown in FIG. 6, the viewing angle $\Theta_{max}$ of a person reaches its maximum at a given temporal frequency Tx. On the other hand, the temporal frequencies indicated by T1 and T2 in FIG. 6 respectively represent a lower limit and an upper limit of dynamic vision coverage range. At a temporal frequency of T1 or less, it is determined that the user is viewing a still image as in FIG. 3, and thus the viewing angle at the time of observing a still image is used. Accordingly, the viewing angle at a temporal frequency of T1 is the viewing angle $\alpha_{max}$ determined by the measurement described with reference to FIG. 3. Likewise, at a temporal frequency of T2 or more, the user cannot correctly recognize a change in the graphic 304 with time, or in other words, the user cannot perform observation properly. Accordingly, in this case, the viewing angle is set to 0° (no field of view). The temporal frequency corresponds to the switching speed of the display of cross-sectional image on the display screen of the display unit 36 (in the case where, for example, the cross-sectional image is switched every two seconds, the switching speed (temporal frequency) is 0.5 Hz).

Up to here, the method for calculating an observed area in step S208 of FIG. 2 has been described with reference to FIGS. 3 to 6. In summary, the method for calculating an observed area when the sight-line stays in the same place and the cross-sectional image is not switched has been described with reference to FIG. 3, the method for calculating an observed area while the sight-line is moving and the cross-sectional image is not switched has been described with reference to FIGS. 4 and 5, and the method for calculating an observed area when the sight-line stays in the same place and the cross-sectional image is switched has been described with reference to FIG. 6.

Viewing angles corresponding to various observing states are obtained by the methods described with reference to FIGS. 3 to 6 in the above-described manner, and stored. Then, in the determination of observed areas in the displayed cross-sectional image (step S208), an observing state at that time is first determined based on the cross-sectional image switching speed obtained in step S204 and the sight-line information (sight-line moving speed) obtained in step S206. Then, a viewing angle corresponding to the determined observing state is obtained from among the stored viewing angles corresponding to various observing states, and a range of the field of view is determined based on the sight-line information (the distance between the user and the display unit 36). Then, in the displayed cross-sectional image, an observed area is determined based on the sight-line information (sight-line position) and the determined range of the field of view. For example, the determined range of the field of view, with the sight-line position being at the center, may be determined as a checked area.

The viewing angle while the sight-line is moving and the cross-sectional image is also switched can be measured by, in principle, combining the method shown in FIG. 4 and the method shown in FIG. 6. To be specific, an observed area can be calculated by measuring a viewing angle when the transparency of the graphic 304 moving at a constant speed described with reference to FIG. 4 is changed with a predetermined temporal frequency as described with reference to FIG. 6. This method, however, requires two variable parameters (the moving speed of the graphic and the period (temporal frequency) of change of the transparency of the graphic), and thus it will take a very long time to measure a change in the viewing angle if this method is actually used. Accordingly, in the present embodiment, a simple method described below is used.

If the cross-sectional image switching speed is greater than T1 and less than T2 (between T1 and T2) in FIG. 6, and the sight-line moving speed is a predetermined threshold value V0 or less, a viewing angle and an observed area are calculated by using the method described with reference to FIG. 6. If, on the other hand, the switching speed is between T1 and T2, and the sight-line moving speed exceeds a predetermined threshold value V0, it means that movement of sight-line and switching of cross-sectional image are taking place simultaneously, and thus it is determined that it is difficult to perform a normal observation. Accordingly, the viewing angle is set to 0°, and the observed area is not set.

FIG. 7 collectively shows the methods for calculating an observed area described above in the form of a list. According to FIG. 7, if the switching speed is a predetermined threshold value or less (T1 or less), the field of view is changed based on the sight-line moving speed, and if the sight-line moving speed is a predetermined threshold value or less (V0 or less), the field of view is changed based on the switching speed. Also, if the switching speed is a predetermined threshold value or more (T2 or more), if the sight-line moving speed is a predetermined threshold value or more (V1 or more), and if the following is satisfied: switching speed>T1 and moving speed>V0, it is determined that there is no field of view (an observable area is not present).

Generally, when a reader or a user wants to efficiently observe a wide range of three-dimensional medical image data, the reader observes the range without much moving his/her sight line while continuously switching the display of cross-sectional image. At this time, the reader is observing a wide field of view including peripheral vision. This state corresponds to the state in which the cross-sectional image switching speed is between T1 and T2, and the sight-line moving speed is V0 or less shown in FIG. 7.

Next, when the reader finds a cross-sectional image in which there is an abnormal shadow, he/she temporarily stops the switching of cross-sectional image so as to thoroughly observe an area (focus area) in which there is the abnormal shadow. In this case, more accurate interpretation is performed with a narrow field of view by using central vision. This state corresponds to the state in which the cross-sectional image switching speed is T1 or less, and the sight-line moving speed is V1 or less, shown in FIG. 7. In this way, by using the methods for calculating an observed area shown in FIG. 7, it is possible to calculate appropriate observed areas corresponding to various image observation methods performed by the reader.

FIG. 8 shows an example of the display screen of the display unit 36 and an example of the installation position of the sight-line detection unit. In FIG. 8, the sight-line detection unit 37 is installed at a position adjacent to a display screen 800 of the display unit 36. In the example shown in FIG. 8, the sight-line detection unit 37 is installed directly below the display screen 800. On the display screen 800, an interpretation start button 802, a marker display button 803, an interpretation end button 804, an image display area 805 and the like are displayed. By the user pressing the buttons, user instructions to start interpretation, display markers, and end interpretation are generated. In the image display area 805, a cross-sectional image selected by a user instruction is displayed.

Also, in the image display area 805, markers representing observed areas are displayed. A marker 806 shown in FIG. 8 shows an example of an observed area observed by the user while switching the display of cross-sectional image. A marker 807 shows an example of an observed area when the user is gazing at a specific area while temporarily stopping the switching of cross-sectional image. Accordingly, the marker 807 is smaller than the marker 806.

Also, in step S212 of FIG. 2, markers are displayed with respect to all observed areas, and thus the marker 806 and the marker 807 are displayed without a distinction therebetween. A configuration may be used in which the marker display attribute (color, shading pattern or the like) is changed each time the user presses the marker display button 803. In this case, the marker 806 and the marker 807 have different display attributes, and thus are displayed with a distinction therebetween.

As described above, with the image diagnosis assistance apparatus according to the present embodiment, the method for calculating an observed area corresponding to the image observation method performed by the reader is used, and it is therefore possible to more accurately determine an observed area according to the observing state of the reader. By providing a visual indication (for example, displaying markers) based on the observed areas determined in the manner described above, it is possible to more appropriately indicate an oversight in interpretation.

Variation 1

The embodiment described above is configured such that the sight-line information of the user viewing the display unit 36 is obtained by using the sight-line detection unit 37 and the sight-line information obtaining unit 45. This variation shows an example in which an observed area observed by the user is determined without using the sight-line detection unit 37 and the sight-line information obtaining unit 45 by assuming that the sight-line of the user is directing toward a predetermined position (for example, the center) of the display unit 36. Hereinafter, the description of the same portions as the embodiment described above is omitted, and different portions will be described.

In this variation, the image diagnosis assistance apparatus 10 does not include the sight-line detection unit 37 and the sight-line information obtaining unit 45, or the image diagnosis assistance apparatus 10 may include these units but does not use them. Due to the sight-line information obtaining unit 45 being absent or unable to be used, steps S206 and S207 of the flowchart shown in FIG. 2 are not performed. Accordingly, in this variation, after execution of step S205, the processing proceeds to step S208. In step S208, the observed area recording unit 46 calculates an area (observed area) in the cross-sectional image observed by the user based on an assumption that the sight line of the user is directing toward the center of the display unit 36. At this time, the observed area recording unit 46 calculates the observed area by using the cross-sectional image switching speed calculated in step S204 and the user sight-line information (the information indicating that the sight-line stays at the center of the display unit 36) based on the above-described assumption.

The method for calculating an observed area is as described with reference to FIG. 3 (the field of view while observing a still image) and FIG. 6 (the field of view when switching the display of cross-sectional image) in the embodiment given above. To be specific, the calculation method when the sight-line moving speed is V0 or less shown in FIG. 7 is used. By doing so, when the display of cross-sectional image is not switched, an area near the center of the display unit 36 (the range of central vision) is determined as the observed area, and when the display of cross-sectional image is switched at a predetermined speed, a wider range (the range of peripheral vision) is determined as the observed area.

As described above, with the image diagnosis assistance apparatus according to this variation, by assuming that the user sight-line is directing toward a predetermined position of the display unit 36, the same effects as in the embodiment described above can be obtained without the use of the sight-line detection unit 37 and the sight-line information obtaining unit 45.

The measurement of visual angle described with reference to FIGS. 3 and 4 may be performed by using the display unit 36 prior to the start of interpretation (S200). By doing so, it is possible to set the observable area according to individual variation of the reader's visual angle.

According to the present invention, it is possible to determine observed areas according to the observing state in which the user views medical images, with higher accuracy.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-181592, filed Sep. 5, 2014, which is hereby incorporated by reference herein in its entirety.

The invention claimed is:

1. An image diagnosis assistance apparatus comprising:
    a display control unit configured to display a plurality of cross-sectional images on a display unit by sequentially switching the plurality of cross-sectional images;
    a first obtaining unit configured to obtain sight-line information regarding a sight line of a user, the sight-line information including position information on a display screen of the display unit;
    a second obtaining unit configured to obtain a switching speed for switching the plurality of cross-sectional images; and
    a determination unit configured to determine an observed area with respect to the plurality of cross-sectional images displayed by the display control unit based on the sight-line information obtained by the first obtaining unit and the switching speed obtained by the second obtaining unit, wherein
    the determination unit increases a size of the observed area as the switching speed increases.

2. The image diagnosis assistance apparatus according to claim 1, further comprising a third obtaining unit configured to obtain a moving speed of the sight line of the user, wherein
    the determination unit changes a size of an observable area that is observed from one sight-line position of the user based on the switching speed and the moving speed.

3. The image diagnosis assistance apparatus according to claim 2, wherein the determination unit changes the observable area based on the moving speed if the switching speed is less than or equal to a first threshold value, and changes the observable area based on the switching speed if the moving speed is less than or equal to a second threshold value.

4. The image diagnosis assistance apparatus according to claim 1, wherein the plurality of cross-sectional images constitute three-dimensional medical image data.

5. The image diagnosis assistance apparatus according to claim 4, wherein the determination unit determines an observed area in the three-dimensional medical image data based on the determined observed area.

6. The image diagnosis assistance apparatus according to claim 1, wherein the determination unit is configured to determine a position of the observed area base on the sight-line information and determine a size of the observed area base on the switching speed.

7. The image diagnosis assistance apparatus according to claim 6, wherein the determination unit is configured to determine a center of the observed area based on a gazing point included in the sight-line information.

8. A control method for controlling an image diagnosis assistance apparatus, the method comprising:
- displaying a plurality of cross-sectional images on a display unit by sequentially switching the plurality of cross-sectional images;
- obtaining sight-line information regarding a sight line of a user, the sight-line information including position information on a display screen of the display unit;
- obtaining a switching speed for switching the plurality of cross-sectional images; and
- determining an observed area with respect to the displayed plurality of cross-sectional images based on the obtained sight-line information and the obtained switching speed, wherein
- a size of the observed area increases as the switching speed increases.

9. A non-transitory computer-readable storage medium storing a program for causing a computer to execute a control method for controlling an image diagnosis assistance apparatus, the method comprising:
- displaying a plurality of cross-sectional images on a display unit by sequentially switching the plurality of cross-sectional images;
- obtaining sight-line information regarding a sight line of a user, the sight-line information including position information on a display screen of the display unit;
- obtaining a switching speed for switching the plurality of cross-sectional images; and
- determining an observed area with respect to the displayed plurality of cross-sectional images based on the obtained sight-line information and the obtained switching speed, wherein
- a size of the observed area increases as the switching speed increases.

10. An image diagnosis assistance apparatus, comprising:
- a display control unit configured to display a plurality of cross-sectional images on a display unit by sequentially switching the plurality of cross-sectional images;
- a first obtaining unit configured to obtain sight-line information regarding a sight line of a user, the sight-line information including position information on a display screen of the display unit;
- a second obtaining unit configured to obtain a switching speed for switching the plurality of cross-sectional images;
- a third obtaining unit configured to obtain a moving speed of the sight line of the user,
- a determination unit configured to determine an observed area with respect to the plurality of cross-sectional images displayed by the display control unit based on the sight-line information obtained by the first obtaining unit and the switching speed obtained by the second obtaining unit, wherein
- the determination unit determines a size of the observed area based on the switching speed,
- the determination unit changes a size of an observable area that is observed from one sight-line position of the user based on the switching speed and the moving speed, and
- the determination unit changes the size of the observable area based on the moving speed if the switching speed is less than or equal to a first threshold value, determines that the observable area is not present if the switching speed is greater than or equal to a third threshold value that is greater than the first threshold value, and changes the size of the observable area based on the switching speed if the moving speed is less than or equal to a second threshold value.

* * * * *